US011576567B2

(12) United States Patent
Rebella et al.

(10) Patent No.: US 11,576,567 B2
(45) Date of Patent: Feb. 14, 2023

(54) OTOSCOPE PROVIDING LOW OBSTRUCTION ELECTRONIC DISPLAY

(71) Applicant: Wisconsin Alumni Research Foundation, Madison, WI (US)

(72) Inventors: Greg Rebella, Hartland, WI (US); James Berbee, Madison, WI (US); Azita Hamedani, Verona, WI (US); Cameron Loper, Falls Church, VA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 780 days.

(21) Appl. No.: 15/856,865

(22) Filed: Dec. 28, 2017

(65) Prior Publication Data
US 2018/0125345 A1 May 10, 2018

Related U.S. Application Data

(63) Continuation-in-part of application No. 14/749,945, filed on Jun. 25, 2015, now abandoned.

(51) Int. Cl.
*A61B 1/227* (2006.01)
*A61B 1/00* (2006.01)
*A61B 1/015* (2006.01)

(52) U.S. Cl.
CPC .......... *A61B 1/227* (2013.01); *A61B 1/00048* (2013.01); *A61B 1/00052* (2013.01); *A61B 1/00082* (2013.01); *A61B 1/00094* (2013.01); *A61B 1/015* (2013.01)

(58) Field of Classification Search
CPC .............................. A61B 1/227; A61B 1/00048

USPC .................................................. 600/179, 200
See application file for complete search history.

(56) References Cited

U.S. PATENT DOCUMENTS

| 4,147,163 | A | * | 4/1979 | Newman | A61B 1/227 320/114 |
| D333,702 | S | | 3/1993 | Hufman | |
| 5,762,605 | A | | 6/1998 | Cane et al. | |
| 6,001,059 | A | * | 12/1999 | Elliott | A61B 1/00087 600/184 |
| 6,106,457 | A | | 8/2000 | Perkins et al. | |
| 6,186,944 | B1 | | 2/2001 | Tsai | |
| 6,221,007 | B1 | | 4/2001 | Green | |
| 6,626,825 | B2 | | 9/2003 | Tsai | |
| 7,354,194 | B2 | * | 4/2008 | Walker | G01J 5/02 374/158 |
| 7,354,399 | B2 | | 4/2008 | Strom et al. | |
| 8,066,634 | B2 | | 11/2011 | Andreassen et al. | |
| 2005/0043588 | A1 | * | 2/2005 | Tsai | A61B 1/07 600/160 |
| 2007/0255108 | A1 | | 11/2007 | Schmitz | |

(Continued)

FOREIGN PATENT DOCUMENTS

EP     1 790 962     5/2007

*Primary Examiner* — Anh Tuan T Nguyen
*Assistant Examiner* — Rynae E Boler
(74) *Attorney, Agent, or Firm* — Boyle Fredrickson S.C.

(57) ABSTRACT

An otoscope provides a circular display allowing a compact housing providing improved simultaneous viewing of the display and the patient's ear for improved positioning and stabilization of the otoscope. A recorded image may be rotationally corrected, and non-image data displayed on the screen may be rotationally corrected with the use of an inclinometer.

20 Claims, 9 Drawing Sheets

(56) References Cited

U.S. PATENT DOCUMENTS

| | | | |
|---|---|---|---|
| 2011/0137118 A1* | 6/2011 | Huang | A61B 1/227 600/109 |
| 2015/0351606 A1* | 12/2015 | Ruppersberg | A61B 1/07 600/200 |
| 2015/0374208 A1 | 12/2015 | Ruppersberg et al. | |
| 2016/0051134 A1* | 2/2016 | Hatzilias | A61B 1/0005 348/65 |
| 2018/0333041 A1* | 11/2018 | Lo | A61B 1/00126 |
| 2019/0046359 A1* | 2/2019 | Hendricks | A61B 1/227 |

* cited by examiner

OTOSCOPE PROVIDING LOW
OBSTRUCTION ELECTRONIC DISPLAY

CROSS REFERENCE TO RELATED
APPLICATION

This application is a continuation in part of U.S. application Ser. No. 14/749,945 filed Jun. 25, 2015, and hereby incorporated by reference.

STATEMENT REGARDING FEDERALLY
SPONSORED RESEARCH OR DEVELOPMENT

--

BACKGROUND OF THE INVENTION

The present invention relates to an otoscope for inspection of the ear and in particular to an otoscope employing an electronic camera insertable into the ear canal.

An otoscope is a medical device allowing a healthcare professional to inspect the ear canal and tympanic membrane (eardrum). A simple otoscope provides for a hollow funnel-shaped speculum whose small end is inserted into the ear canal. The purpose of the funnel shape of the speculum is to provide a visual path to the tympanic membrane and to assist in controlling depth of insertion of the speculum. Modern otoscopes include an internal source of illumination directed down the speculum axis from a contained battery-operated lamp and may provide a magnifying lens supported outside the ear and aligned with the axis of the speculum to provide an enlarged image of the ear structure being viewed. More recently, otoscopes have incorporated digital cameras with displays directly on the otoscope for viewing the camera image. An example of these otoscopes is found in U.S. Pat. No. 9,326,668 hereby incorporated by reference.

The use of an otoscope requires that the clinician attend carefully to the positioning of the otoscope throughout the examination. The clinician must both hold the otoscope and stabilize it against the patient's head with one hand, while the other hand manipulates the external ear to maximize "straightness" of the external auditory canal. Once the visual axis is properly aligned, a single user is able to view and assess the characteristics of the tympanic membrane.

The use of an otoscope, particularly with infants, requires that the healthcare professional pay constant attention to placement and positioning of the otoscope by observing the infant's outer ear and at times using one hand to both hold the otoscope and stabilize the otoscope against the infant's head while the other hand manipulates the external ear to maximize "straightness" of the external auditory canal. Desirably, the camera display for the otoscope is mounted on the otoscope itself to minimize the need for the healthcare professional to look away from the otoscope and patient to see the desired clinical information. Nevertheless, the necessary size of display needed to provide proper readability and resolution can often in such cases obstruct the healthcare professional's view of the patient during this positioning and bracing operation if the healthcare professional simultaneously wants to view the display. This can be a particular problem when the otoscope is rotated, for example, with a handle positioned laterally rather than vertically, for improved bracing or access to the patient.

SUMMARY OF THE INVENTION

The present inventors have recognized that because the region of interest of the image acquired by an otoscope is largely circular, by using a matching circular display that is directly aligned with the visual axis of the camera tip, the obstructive qualities of the display can be greatly minimized over a range of different otoscope orientations, thus improving the ability to simultaneously view the display and the patient's external ear. The net effect is to allow the clinician to have greater dexterity and maximize comfort during the otoscopic examination.

In different embodiments, the invention may also provide a disposable, clean, sheath (speculum) for an otoscope of a type having a tip-mounted camera and light source. Such tip-mounted cameras and light sources create substantial risk of blinding internal reflection when covered by a window. By providing a speculum with a window that may be pulled tightly against the light sources and camera, such intentionally blinding internal reflections are reduced or eliminated while providing a clean barrier between the otoscope and patient.

In different embodiments, the invention may provide a structure allowing the otoscope to be adapted to commonly available otoscope bases. This adaptation may employ a locking collar that overrides rheostat systems used for normal incandescent lamp otoscopes allowing the innovative otoscope of the present invention to be readily adapted to legacy examination rooms.

In different embodiments, the invention can provide an audio commands to the otoscope camera to obtain a "snapshot" eliminating the need for a manually operated button that could cause the healthcare professional to inadvertently reposition the otoscope while an image is being acquired.

Specifically, then, in one embodiment, the invention provides an otoscope having a housing adapted for support by a hand of a healthcare professional. An elongate probe element having a proximal end supported by the housing provides a distal end that may extend along an axis into the ear canal. The distal end of the elongate probe may support an electronic camera for viewing into the ear canal communicating with a circular electronic display displaying an otoscope image from the camera and spaced from the distal end of the elongate probe along the axis and centered along the axis.

It is thus a feature of at least one embodiment of the invention to provide the benefits of electronic display, including magnification, image stabilization, and brightness and contrast adjustment, while preserving the observing healthcare professional's ability to fully view the outer ear to assist in alignment and stabilization of the otoscope. A circular display maximizes the useful display area while minimizing the obstructive nature of the display particularly when the otoscope is used with the handle rotated from a vertical position.

The display may be circumscribed by a cone having an apex at the distal end of the probe and a conical angle of less than 45 degrees and/or may have a diameter that extends less than three inches from the axis at all angles about the axis.

It is thus a feature of at least one embodiment of the invention to optimize trade-off between display readability and minimizing display obstruction.

The processor may execute a stored program for displaying non-image data in a peripheral ring about the image.

It is thus a feature of at least one embodiment of the invention to permit the simultaneous display of image and non-image data on a single display to minimize the need for the healthcare professional to avert his or her eyes from the display and patient, while positioning the data in a location of the image having, a priori, less clinical significance.

The non-image data may include an arcuate bar display whose angular extent indicates data.

It is thus a feature of the invention to provide an intuitive compact graphic that works well in the periphery of the circular display.

The circular electronic display may provide a touchscreen for sensing touches on a surface of the circular electronic display wherein the arcuate bar display represents a video sequence of images taken from the electronic camera and wherein a touch along the arcuate bar display selects an image from the video sequence for display.

It is thus a feature of at least one embodiment of the invention to provide an extremely compact method of indexing through a video sequence allowing the healthcare professional to capture the best image therefrom, for example, when imaging an agitated or juvenile patient.

The display may indicate a left or right ear being imaged as linked to the image.

It is thus a feature of at least one embodiment of the invention to ensure recorded images clearly indicate which ear was being imaged in the image record.

The otoscope may further include an electronic inclinometer for changing the orientation of at least one of the displayed non-image data and recorded image data according to a deduced gravitational vector.

It is thus a feature of at least one embodiment of the invention to maximize the readability of non-image data during use of the otoscope and to maximize the interpretability of image data reviewed at a later time by clearly indicating the orientation of that data.

The housing may provide a display portion holding the electronic display and elongate probe, and a handle portion extending away from the axis to be held by a healthcare professional, and the display portion may be mechanically and electrically releasably attachable to the handle portion by means of a twist lock coupling.

It is thus a feature of at least one embodiment of the invention to integrate smoothly with existing examination room equipment intended for conventional otoscopes having a twist lock connector.

The handle portion may provide a rheostat controlling electrical power delivered to the display portion and the handle portion may provide a collar fitting over the rheostat to prevent movement thereof.

It is thus a feature of at least one embodiment of the invention to disable the rheostat found on conventional otoscopes to prevent an inadvertent reduction in electrical power during use of the otoscope.

The collar portion may include a rheostat engagement surface turning the rheostat to a full power position with rotation of a twist lock coupling for engagement.

It is thus a feature of at least one embodiment of the invention to promote a full power position of the rheostat when the otoscope is assembled to a pre-existing legacy handle.

The invention may also provide for a speculum for an otoscope having an in-ear camera providing a replaceable tubular sheath sized to fit within in the ear canal and to receive the elongate probe element therein, the distal end of the tubular sheath providing a transparent window covering permitting imaging therethrough and a proximal end of the tubular sheath providing a connection to the housing creating a spring biasing of the window against the distal end of the probe element.

It is thus a feature of at least one embodiment of the invention to permit a protective covering of the camera from cross-contamination with the patient using a window layer without creating image degradation caused by the close proximity of an intense light source and the camera in the narrow tip of the probe.

In one embodiment, the distal end of the tubular sleeve maybe covered by an elastic cot and the proximal end of the tubular sheath may stretch the elastic cot over the electronic camera to provide a transparent covering of the camera allowing imaging therethrough.

It is thus a feature of at least one embodiment of the invention to provide a close abutment of the window against the camera and light sources (to minimize internal reflections and maximize image quality) while providing an easily fabricated low-aberration window formed in part by the stretching process.

The invention may in addition or alternatively provide a speculum having a tubular sheath sized to fit within in the ear canal to receive an elongate otoscope probe element therein wherein a distal end of the tubular sleeve provides a tool extending axially beyond the distal end of the probe element for engaging objects within the ear within the field of view of the camera. In this manner, ear wax and foreign bodies may be removed safely under direct visualization.

It is thus a feature of at least one embodiment of the invention to provide a disposable scraper tool integrated into the disposable speculum and positioned proximate to the camera for improved positioning and manipulation.

The tool element may be malleable to be formed into a curve after manufacture with respect to the axis and to retain that curvature.

It is thus a feature of at least one embodiment of the invention to provide an extremely versatile tool that can be modified by the healthcare professional as needed for a particular situation and that better nests for efficient shipping.

The tool element may provide a scoop communicating with a channel connectable to a vacuum source.

It is thus a feature of at least one embodiment of the invention to provide a suction tool closely located to the camera for accurate control of that suction tool.

The otoscope may provide a processor operating in a first mode to provide a dynamic image on the display indicating the view from the electronic camera and in the second mode, triggered by a user's voice received by the microphone, to capture a static image on the display indicating the view from the electronic camera at the time of the voice command.

It is thus a feature of at least one embodiment of the invention to allow capture of an image without disrupting the orientation of the otoscope as may occur during the activation of a physical button or touchscreen by the user's hand.

These particular objects and advantages may apply to only some embodiments falling within the claims and thus do not define the scope of the invention.

DETAILED DESCRIPTION OF THE PREFERRED EMBODIMENT

First Embodiments

Figure 1:
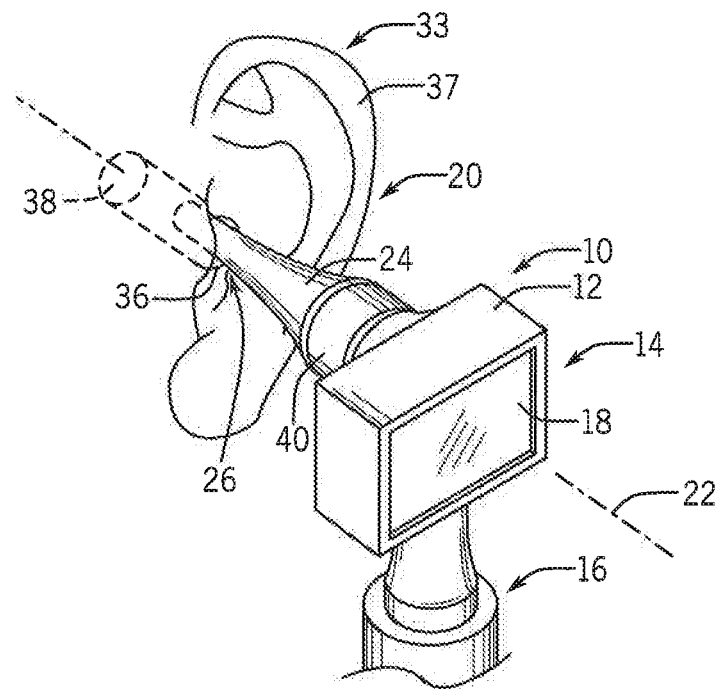
FIG. 1 is a perspective view of an otoscope constructed according to the present invention providing a housing presenting on a front side an electronic display and on a rear side having a camera on a probe element extending away from the electronic display for insertion into the ear canal and covered by a disposable speculum.

Referring now to FIG. 1, an otoscope 10 of the present invention may provide a housing 12 having a head portion 14 and a detachable grip portion 16. The grip portion 16 is sized to be grasped by the hand of a healthcare professional in the manner of a conventional otoscope with the grip portion 16 extending generally upward from the healthcare professional's hand to the head portion 14.

A front surface of the head portion 14 may provide for an electronic touchscreen display 18, for example, being a backlit three-color liquid crystal display (LCD) of a type known in the art having a touch surface and decoder. An elongate probe assembly 20 may extend from a rear face of the head portion 14 in a direction away from the display 18 along an axis 22 normal to the surface of the display 18. The probe assembly 20 may include a generally conical speculum 24 constructed at least in part of the transparent thermoplastic material to provide for light conducting properties as will be described below.

As is generally understood, the outer ear 33 of a human patient includes the pinna 37 providing a sound collecting structure. The pinna 37 surrounds an ear canal 36 leading to and terminating at the tympanic membrane or eardrum 38. A length of the ear canal 36 in an average adult human is approximately 2.5 centimeters and the ear canal 36 has an average diameter of approximately 0.7 centimeters.

Figure 2:
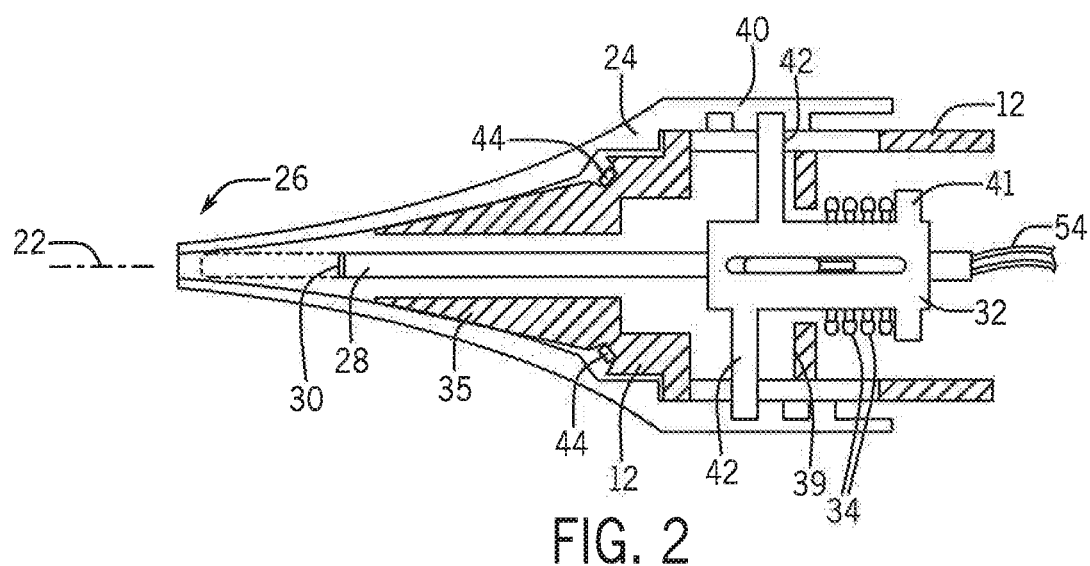
FIG. 2 is an elevational cross-section through the probe element and the disposable speculum showing a mechanism for retracting the probe element and camera when the speculum is removed and extending the probe element and camera when the speculum is in place.

Referring now also to FIG. 2, the speculum 24 may taper inward as one moves away from the head portion 14 to a distally located distal tip 26. The speculum 24 provides a central bore which holds an extendable cylindrical probe 28 having on its distal tip a front facing electronic camera 30 for acquiring multi-pixel, three-color images in a field of view directed along the axis 22. Electronic camera 30 may, for example, be a self-contained charge coupled device (CCD) camera such as is commercially available providing, for example, a measurement area of 1.4 mm diagonal and 62,500 pixels.

A proximal end of the cylindrical probe 28 is supported by a spring-loaded slider 32 that may move along the axis 22 with respect to structure of the housing 12 generally constrained for translational motion only. A helical compression spring 34 may extend between an inwardly extending flange 39 of the housing 12 and a rearward radially outwardly extending flange 41 on the slider 32 to bias the slider 32 in a retraction direction withdrawing the camera 30 within a protective sleeve 35. The sleeve 35 is fixed with respect to the housing 12 and surrounds the camera 30 for protection when the camera 30 is fully retracted.

A proximal end of the conical speculum 24 may provide for a collar 40 having internal threads that can engage outwardly extending pins 42 of the slider 32. Clockwise rotation of the collar 40 (looking toward the proximal end) pulls the pins 42 forward toward the distal tip 26 of the speculum 24 while pulling the speculum 24 onto the housing 12. Forward motion of the pins 42 moves the slider 32 forward against the force of the spring 34 extending the camera 30 to a position proximate to the distal tip 26. Thus, the fragile camera 30 is exposed only when the protective speculum 24 is in place. A detent feature on the housing 12 (not shown) may lock the collar 40 against dislodgment or, alternatively, friction provided by the force between the internal threads and the pins 42 may serve the same purpose.

Figure 3:
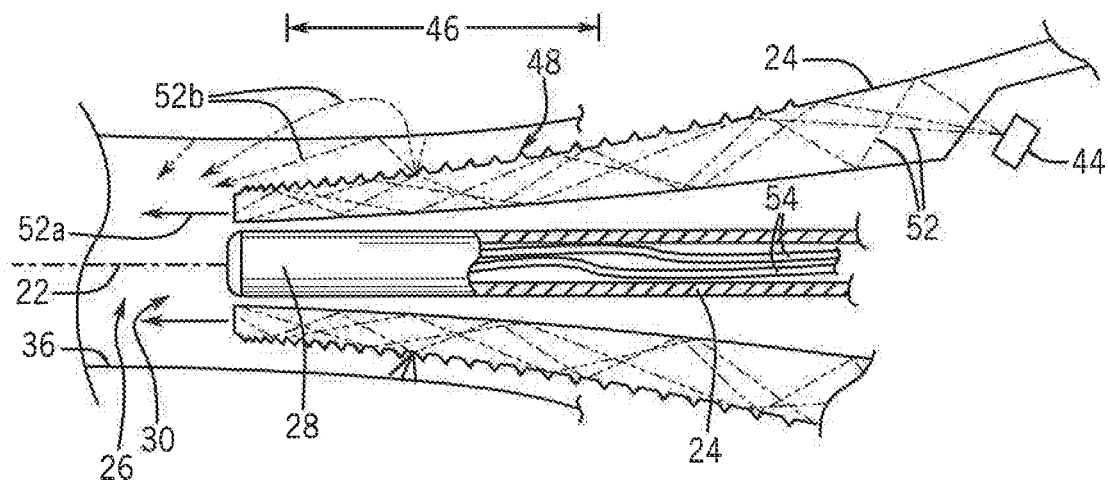
FIG. 3 is a detailed fragmentary view of FIG. 2 with the camera element fully extended showing radial and axial illumination of the ear canal such as creates a diffuse lighting for better resolving the ear structure.

Referring now also to FIG. 3, all or part of the speculum 24 may be constructed of a transparent material so that light emitting diodes 44 mounted on the structure of the housing 12 may project light 52 into a proximal portion of the conical speculum 24. From there, the light 52 may be conducted by internal reflection in the manner of a light pipe to the distal tip 26 of the conical speculum 24. The light emitting diodes 44, as attached to structure of the housing 12, will be retained when the conical speculum 24 is removed and may be oriented to face a feature on the conical speculum 24 that promotes coupling of light 52 from the LEDs 44 into the conical speculum 24, for example, an optical flat perpendicular to the direction of light propagation. In alternate embodiments, the light emitting diodes 44 may couple to fiber optics within the speculum 24.

In one embodiment, the LEDs 44 may provide for a combination of red, green, and blue elements so that the hue of the project light 52 from the LED 44 may be controlled, for example, to accentuate certain ear structure. At the distal tip 26 a portion of light 52a exits in a direction parallel to the axis 22; however, some light 52b in a distal region 46 of the speculum 24, before distal tip 26, may be coupled by a diffusing roughness 48 on the outer surface of the speculum 24 out of the speculum 24 to provide light 52b emanating along a radial direction from the speculum 24 to strike the walls of the ear canal 36. This light 52b, through reflection and scattering between the outer surface of the speculum 24 and the walls of the ear canal 36 and through internal conductance to the tissue of the ear canal 36, provides diffuse multi-angle illumination of the ear structure in the ear canal providing improved viewing of that structure through more uniform illumination and illumination arriving at multiple angles. The region 46 may be, in one embodiment, five millimeters in length along the axis 22 and as much as one and a half centimeters in some embodiments.

Figure 4:
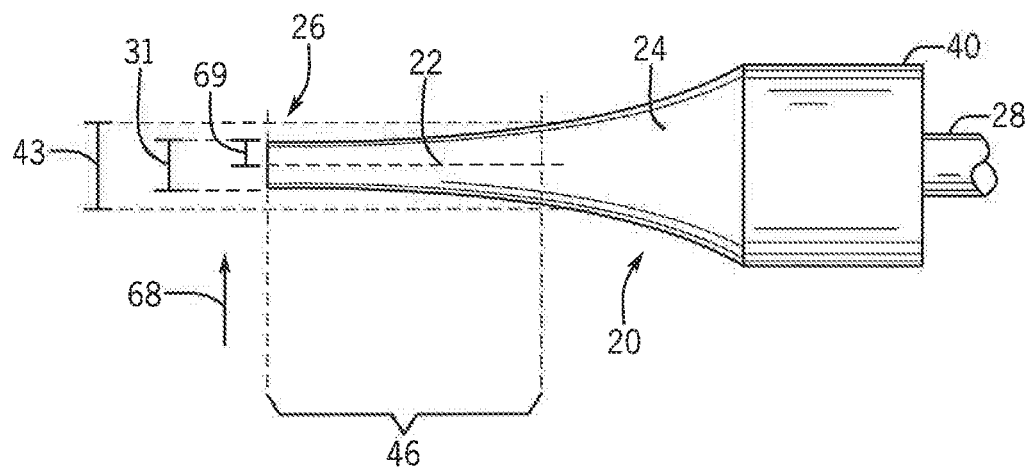
FIG. 4 is a side elevational view of the speculum installed on the probe element showing flexibility of the combined assembly.

Referring now to FIG. 4, the diameter 31 of the distal tip 26, measured in a plane perpendicular to the axis 22, may be less than two millimeters and the diameter 31 of the speculum 24 in the distal region 46, extending from the distal tip 26 along the axis 22 by at least five millimeters and in one embodiment one centimeter, may be less than five millimeters and in some embodiments less than three millimeters to be substantially smaller than the ear canal 36. It is intended that the speculum 24 that surrounds the camera 30 be sized to allow imaging of the eardrum 38 past minor obstructions, such as normally present earwax, and to allow passage within the ear canal 36 by medical instruments such as a curette for removing obstructing bodies such as earwax while probe assembly 20 is in place for imaging, that is, to permit instruments to extend to the side and pass the end of the distal tip 26.

Referring still to FIG. 4, as noted above, the present invention provides a distal tip 26 that is more flexible than a typical otoscope speculum. Generally, the flexibility of the distal tip 26 is intended to improve the comfort to the patient and reduce risk of damage to structure of the outer ear 33 caused by a small diameter probe. When the head portion 14 is stabilized, a perpendicular force 68 applied to the distal end of the distal tip 26 of 100 grams will cause a deflection 69 of no less than one millimeter. In contrast, a similar force applied to the end of the atypical speculum will provide a corresponding deflection at the end of the speculum of much less than one millimeter. It will be appreciated that this flexibility may be provided by constructing the cylindrical probe 28 and conical speculum 24 from a flexible material or by mounting the cylindrical probe 28 and conical speculum 24 to the housing 12 through a flexible or compliant mount that allows a tipping of these elements in response to applied lateral force, or by a coating of the cylindrical conical sheath by elastomeric material, or by a combination of these approaches.

Figure 5:
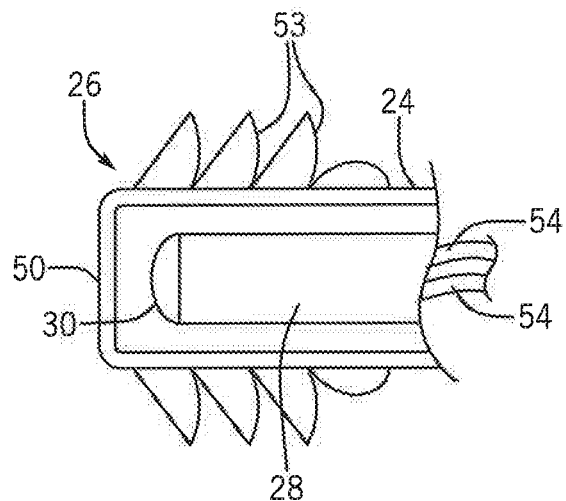
FIG. 5 is a detailed cross-section of the distal end of FIG. 4 showing radial teeth on the speculum for assisting in the removal of foreign material from the ear canal and showing a lens protector incorporated into the disposable speculum.

Referring now to FIG. 5, the distal tip 26 of the speculum 24 may be closed by an optically transparent, low distortion window 50 allowing images to be detected therethrough while protecting the camera 30 from contamination while also providing a clean shield between the camera 30 and patient. An outer surface of the speculum 24 proximate to the distal tip 26 may include rearwardly canted bristles or teeth 53 that may serve the purpose of assisting in the removal of debris and material from the ear canal 36 using the speculum 24 itself. These teeth 53 may be formed simultaneously with the material of the speculum 24 to be optically clear and therefore to pass illumination. Alternatively, the teeth 53 may be overmolded of a flexible elastomeric material such as silicone rubber thereby serving also to reduce the pressure between the distal tip 26 and the ear canal 36 by a cushioning operation.

The cylindrical probe 28 may be constructed of a relatively flexible material such as a silicone or polyvinyl chloride material and may be tubular to provide a passage for electrical conductors 54 communicating pixel image data from the camera 30.

Figure 6:
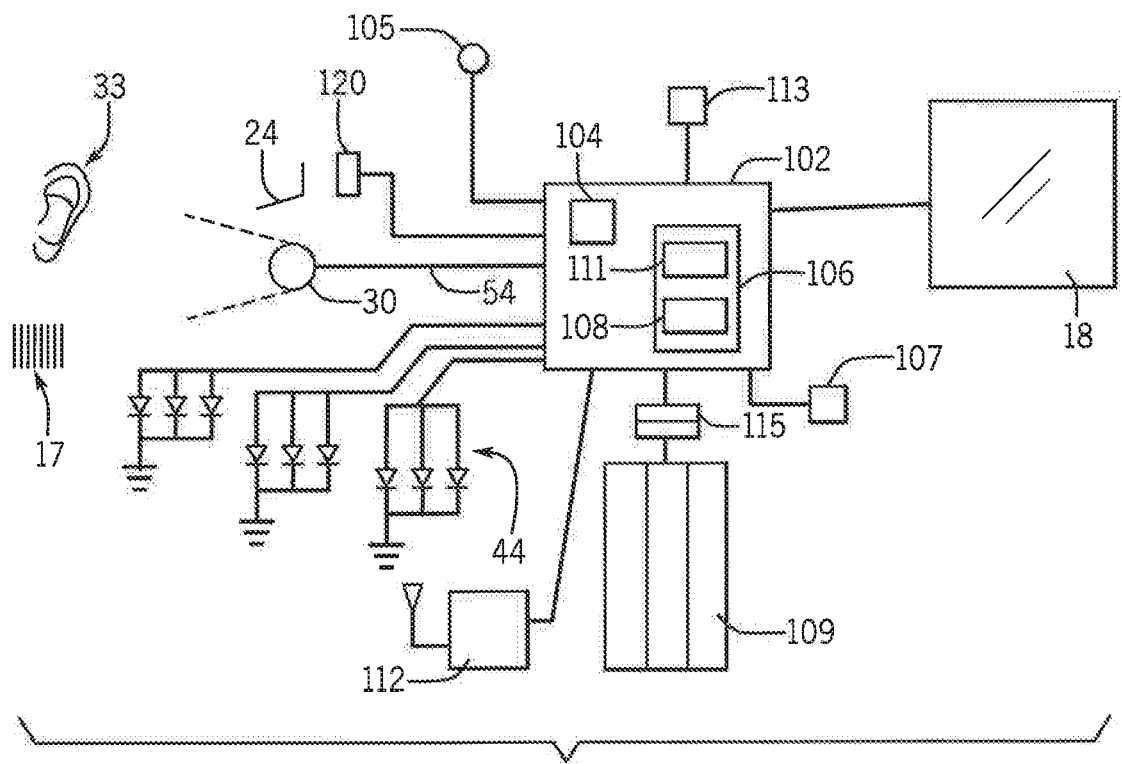
FIG. 6 is a simplified block diagram of the electronics of the otoscope of FIG. 1.

Referring now to FIG. 6, the otoscope 10 may incorporate an electronic controller 102 such as a microcontroller being in essence an electronic computer and I/O circuitry. The controller 102 will provide a processor 104 communicating with a memory 106 permitting non-transient storage of a program 108. Generally, the program 108 will provide for the receipt of signals from the camera 30 for presentation on display 18 of images from the camera 30 and will provide for transmission of such images to affiliated equipment, for example, a PACS device. Program 108 may perform normal image processing, for example, exposure control, contrast adjustment, color balance, motion stabilization, image rotation and the like. The program 108 through the controller 102 may also control the illumination of the LEDs 66 as part of the exposure control process. In addition, the memory 106 may hold a barcode decoder program 111 allowing the otoscope 10 to also be used for reading data from barcodes 117, for example, to identify a particular image to a particular patient's file and transmit that barcode data with images in a protocol for linking the two.

The controller 102 may also communicate either through a wireless transceiver 112 or an electrical connector 114 with other devices, for example, to permit the transmission of image data and barcode data to a remote electronic medical record server.

A power button 113 may communicate with the controller 102 to put electronic circuitry into a low power sleep state, disabling the display 18, camera 30, and LEDs 66.

The program 108 in a standby mode may cycle through different colors on the LEDs 44 or display particular colors (e.g., pink) to improve the attractiveness of the otoscope 10 for pediatric patients who may be fearful of medical equipment. The otoscope circuitry described above may be powered by a battery 109 contained in a grip that may be removably connected to the housing 12 by electrical and mechanical connector 115. Alternatively, the electrical and mechanical connector 115 may allow attachment of the otoscope 10 to a handle unit attached to a wall transformer or the like generally understood in the art such as are used in many examination rooms.

A sleeve detector switch 120 may also be provided to detect whether speculum 24 is in place before activating the otoscope 10 to prevent use of the otoscope 10 without a protective speculum 24.

Figure 7:
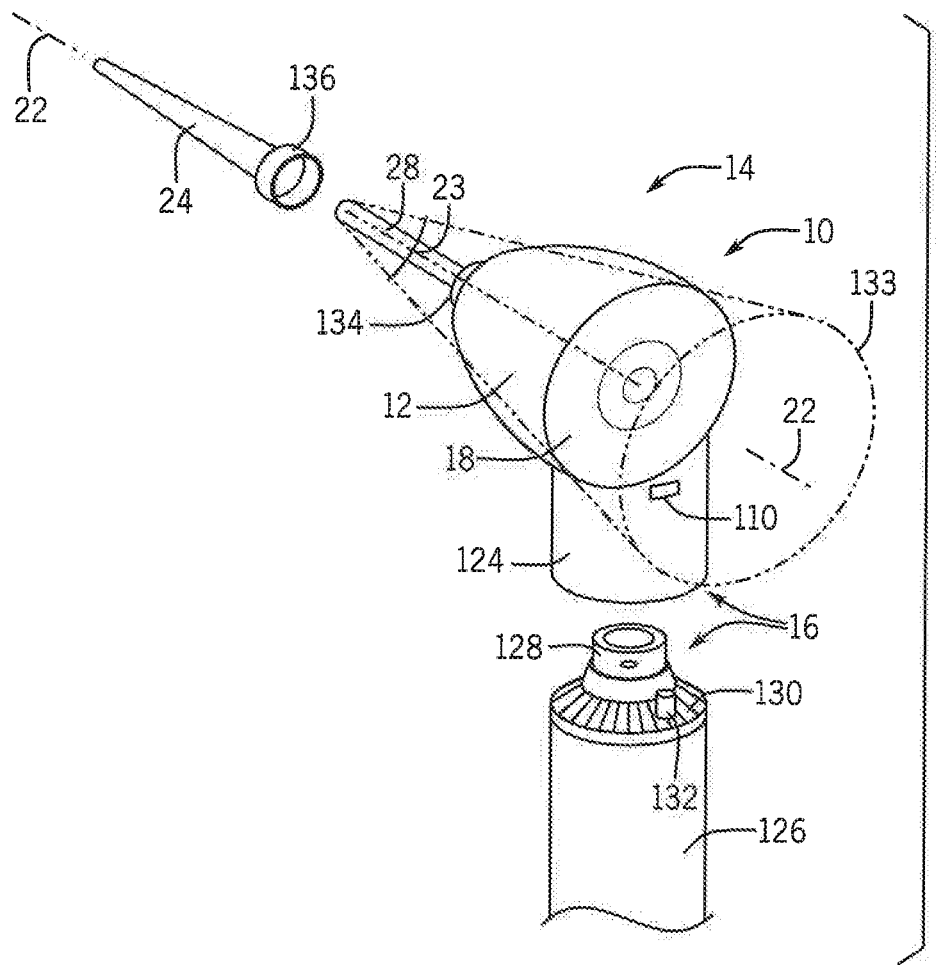
FIG. 7 is a figure similar to FIG. 2 showing an alternative otoscope design providing a circular display and improved visualization of the outer ear when the healthcare professional is viewing the display and further showing a releasable power handle.

The controller 102 may also communicate with a microphone 105, for example, exposed through a microphone grate 110 shown in FIG. 7. In this respect, the controller 102 may provide for simple speech recognition properties, for example, allowing the healthcare professional to take a snapshot using the otoscope 10, for example, by saying a keyword such as "snapshot". An example speech recognition core suitable for use with the present invention is the Texas instrument C5535 or C5534 devices commercially available from Texas instruments Corporation.

A MEMs type inclinometer 107, for example, in the form of a three-axis accelerometer or accelerometer/gyroscope or similar device, may be used to detect the rotational orientation of the housing 12 about the axis 22 which will be used to provide rotational correction of the image as will be discussed below.

As will be discussed in greater detail below, the controller 102 may receive data from the camera 30 and provide for image processing such as contrast and brightness adjustment, image stabilization and magnification and may display the image together with salient other non-image data based on battery charge, video sequence, etc. on the touch screen display 18 while communicating with the various components discussed above using a stored program. The camera 30 may obtain a regular sequence of images in a video stream to be stored in the memory 106 or may store or mark selected snapshot images under control of the user as will be discussed below.

It will be appreciated that the speculums 24 are constructed to be relatively low-cost and therefore disposable, for example, such as may be manufactured by injection molding, and in this regard a variety of different sleeve types may be provided, for example, having different teeth designs for different purposes including other medical inspection of the nose or the like.

Second Embodiment

Referring now to FIG. 7, the display 18 may be circular in outline having a diameter of approximately 1.5 inches and less than two inches and desirably less than 2.5 inches. The display 18 may be centered on the axis 22 having a viewable face perpendicular to that axis 22 so that the display 18 is subtended by a right circular cone 133 having its apex at the distal end of the cylindrical probe 28 and its base perpendicular to the axis 22. This subtending cone 133 may have a vertex angle 23 of less than 60 degrees and ideally less than 45 degrees to provide an improved ability by the healthcare professional to visualize the outer ear 33 (shown in FIG. 1) around the display 18 and the housing 12.

The grip portion 16 may include a downwardly extending grip collar 124 connecting the head portion 14 with a removable power handle 126 that may fit within the collar 124 and lock to the housing 12 with a quarter turn of the power handle 126. In this regard, the power handle may have an upwardly extending electrical and mechanical connector 128 received by a corresponding connector within the collar 124. Surrounding the connector 128 is a rheostat operator 130 whose rotation changes the voltage delivered by the handle 126 to the remainder of the head portion 14. A lock button 132 may protrude upward from an edge of the rheostat operator 130 to be depressed before the rheostat operator 130 may be rotated from an off position to increase the power to the connector 128 from zero voltage to an operating voltage. The handle 126 may provide for internal rechargeable batteries or may be connected by a cable extending from the bottom of the handle 126 (not shown) connecting the handle 126 to a wall transformer or the like.

Figure 8:
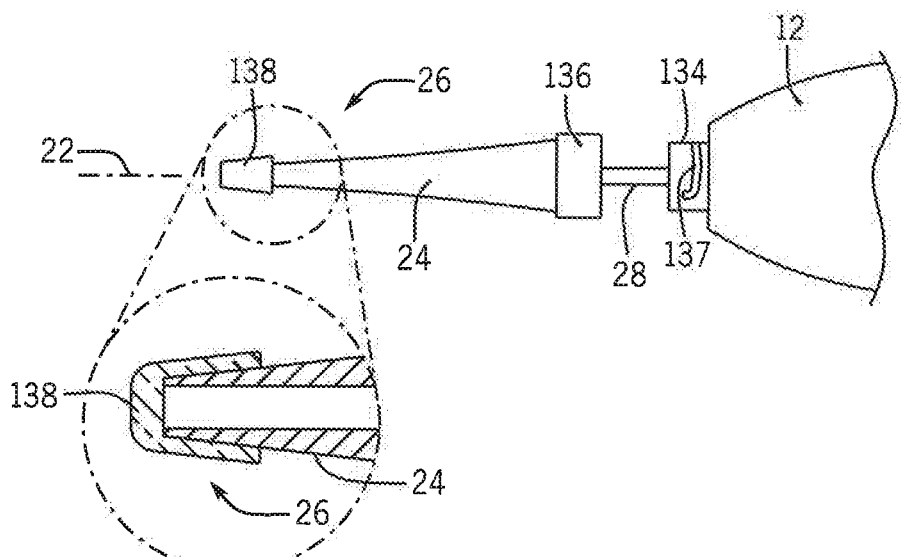
FIG. 8 is a side elevational fragmentary view of the embodiment of FIG. 7 showing a replaceable clean speculum being partially installed on the otoscope and having an elastomeric window material at a distal end of the speculum.

Referring now also to FIG. 8, a removable speculum 24 may fit over the probe 28, the latter attached to the head portion 14 of the housing 12, by a quarter turn twist lock engagement between a cylindrical mounting boss 134 on the housing 12 and the tubular speculum collar 136. As is understood in the art, such a quarter turn collar 136 allows slidable installation of the speculum 24 over the probe 28 and into engagement with the mounting boss 134, the former having a radially inwardly extending tooth received within a corresponding outer peripheral helical groove 137 around the outside of the cylindrical boss 134. This helical groove 137 spirals away from the distal end of the probe 28 for approximately 90 degrees and then returns a short distance in the opposite direction to provide a detent stop point. A locking is provided because of a spring biasing tending to push the locking collar 136 away from the housing 12 either from interference between the speculum 24 and the housing 12 or the probe 28 and the speculum 24 as will be discussed below.

Generally, the body of the speculum 24 may be in the form of a hollow trumpet tapering downward toward the distal tip 26, for example, constructed of a rigid thermoplastic integrally molded to the collar 136. This rigid material allows the speculum 24 to easily slide over the probe 28 without the resistance that might be expected for example if this material were an elastomer. A transparent elastomeric material 138 may be overmolded to the speculum 24 to hermetically seal that the distal tip 26 of the probe 28 against contamination from the environment of the ear and vice versa.

Figure 9:
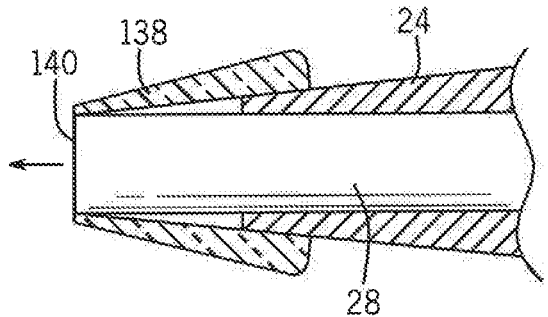
FIG. 9 is a side elevational cross-section in a vertical plane of the distal end of the clean speculum of FIG. 8 showing a stretching of the elastomeric material to provide a tight spring-biased window against the distal end of the probe.

Referring now to FIG. 9, the length of the speculum 24 is set so that when the locking collar 136 is fully installed on the cylindrical boss 134, the distal end of the probe 28 presses outward on the elastomeric material 138 stretching it and thinning it to improve its transparency and reduce optical aberration therethrough by means of the naturally evening property of the stretching of elastomeric material. During the stretching process, the elastomeric material 138 remains adhered to the end of the speculum 24 preserving a clean isolation between the ear and the probe 28. Elasticity of the elastomeric material 138 provides the spring biasing promoting engagement of the lock between the collar 136 and boss 134 and also pulls the elastomeric material 138 into a window 140 closely abutting against the end of the probe 28 to reduce internal reflections.

Figure 10:
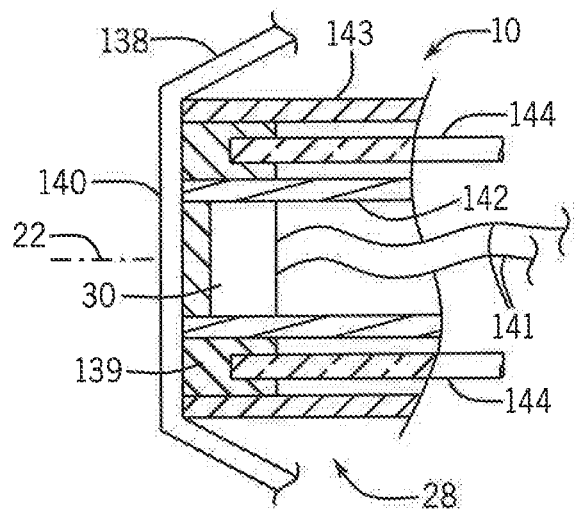
FIG. 10 is a side elevational cross-section through the distal end of the probe showing a positioning of a camera and peripheral fiber optic light sources segregated so as to minimize internal reflections when coupled with a spring-biased front window of the replaceable speculum; a FIG. 11 is a perspective view of an alternative speculum having an axially extending scraper.

Referring momentarily to FIG. 10, the outer wall of the probe 28 may be formed by an outer tube 143 holding a second coaxial tube 142. Within the second coaxial tube 142 is the camera 30 oriented to look along axis 22. The second coaxial tube 142 serves to block light transmitted by optical fibers 144 from passing laterally to the camera 30, the optical fiber's 144 position preferably aligned with axis 22 between tube 142 and the outer tube 143 of the probe 28. Both the optical fibers 144 and the camera 30 may be embedded in an optically transparent epoxy material 139 and have rearward conductors 141 for camera electrical signals. The window 140 of elastomeric material 138 is pulled tight against the ends of these tubes 143 and 142 eliminating the gap that would permit internal reflection off of the inner surface of the window 140 from the optical fibers 144 to the camera 30 such as would blind the camera 30 if the window 140 were spaced loosely away from the end of the tubes 142 and 143. A similar effect may be obtained without the inner tube 142 by placing the optical fibers or the camera 30 directly at the edges of the tube 143 so that there is no gap in which an optical internal reflection can occur. In this case, the optical fibers 144 may communicate with LEDs 44 being either a set of colored LEDs or one or more high-intensity white LEDs.

In an alternate embodiment (not shown), the window 140 may be constructed of a rigid material, for example, using a thermoforming process or injection molding process to form the speculum 24 and window 140 either separately or as assembled components, so that the window 140 is nevertheless pulled closely against the end of the tube 142 to prevent light reflection between the bright light source and the camera 30 through the presence of the window 140. By managing intense internal reflection, the invention allows a complete covering of the probe to reduce cross-contamination.

Figure 11:
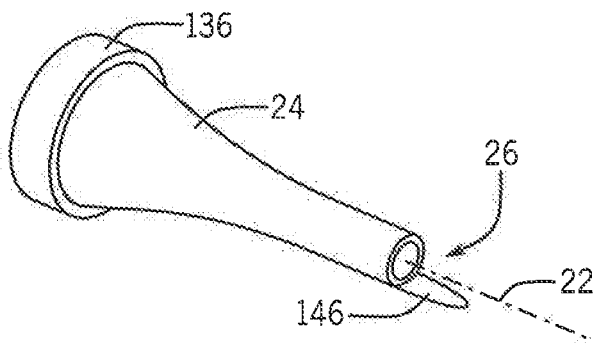
Figure 12:
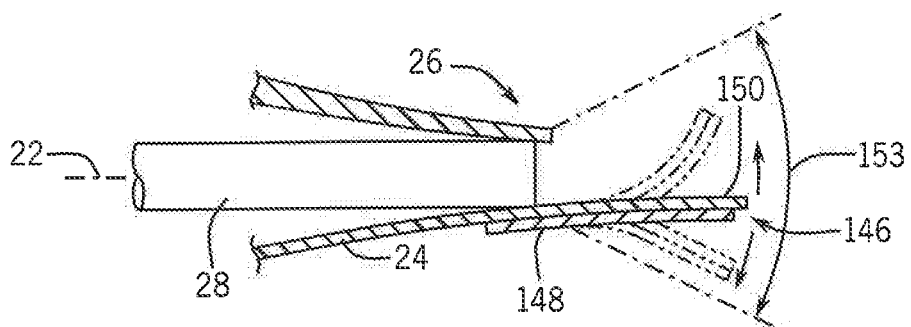
FIG. 12 is a side elevational perspective along a vertical plane of the distal end of the speculum of FIG. 11 showing a laminated soft metal element providing a malleable and reshapeable scraper.

Referring now to FIGS. 11 and 12, in an alternative embodiment, the speculum 24 may have at its distal tip 26 a scraper 146 extending parallel to the axis 22 from a side wall of the of the speculum 24 at a periphery around the circular orifice in the speculum 24 exposing the distal end of the probe 28. The scraper 146, for example, may extend from the end of the probe 28 by ⅛ to ½ inch in a preferred embodiment. The scraper 146 may, for example, be pre-curved toward or away from the axis 22 or in a preferred embodiment may be parallel to the axis 22 for general use and for improved shipping in which the speculums 24 are nested. In this latter case, the scraper 146 may include a ductile metal layer 148 alone or laminated to a flexible thermoplastic layer 150 allowing a curvature to be formed in the scraper 146 by the healthcare professional for particular application by a simple bending process of the scraper 146 where the ductile metal layer 148 retains that curvature after bending. Generally, curvature is possible within a field of view 153 of the camera 30 within the probe 28 (about 50 degrees) permitting use of the scraper 146 to be visualized during use.

Figure 13:
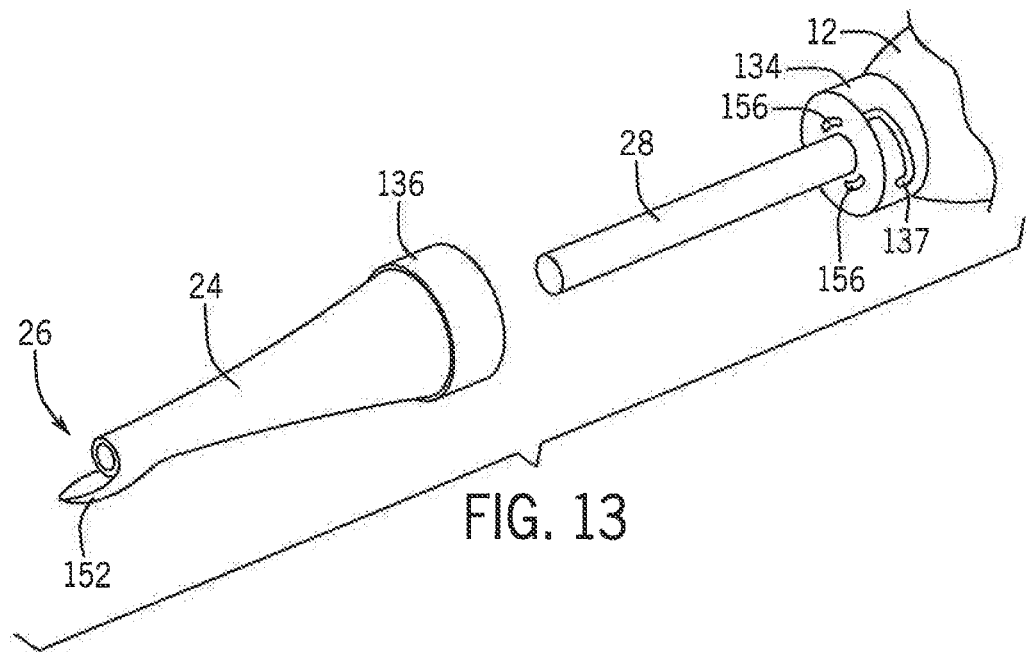
FIG. 13 is an exploded diagram showing an alternative speculum having a vacuum scoop for communicating with a corresponding port on the otoscope.
Figure 14:
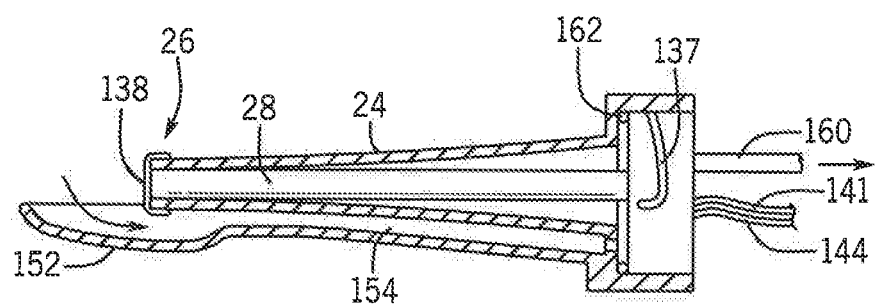
FIG. 14 is a cross-sectional view along a vertical plane through the speculum and assembled otoscope of FIG. 13.

Referring now to FIGS. 13 and 14, in an alternative embodiment, the speculum 24 may have at its distal tip 26, a scoop 152 extending, like the scraper 146 of FIG. 11, parallel to the axis 22 from the side wall of the speculum 24 at a periphery around the circular opening in the speculum 24 exposing the distal end of the probe 28. The scoop 152 may be positioned to the side of the distal end of the probe 28 to extend beyond the distal end of the probe 28 and face inward over the front of the probe 28. The scoop 152 may communicate via an internal channel 154 within the speculum 24 that may connect to air ports 156 in the front face of the boss 134, the ports 156 leading to a source of vacuum via conduit 160, allowing the speculum 24 to be used to aspirate debris and the like through the scoop 152. In this case, the collar 136 may support on its inner face an O-ring 162 providing a seal against the front face of the boss 134 to prevent leakage of air through the proximal end of the sheath and its interface with the boss 134. As will be discussed below the source of vacuum connected the conduit 160 may be either an external vacuum line connected to the housing 12 or an internal vacuum pump system as will be discussed.

Figure 15:
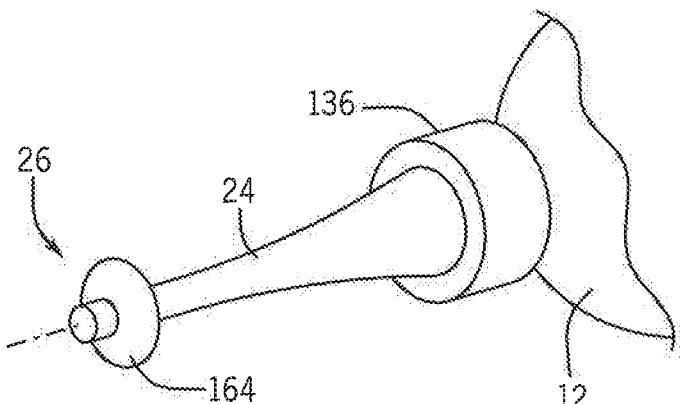
FIG. 15 is a perspective view of an alternative design of the speculum providing an inflatable collar for the removal of obstructions from the ear canal.
Figure 16:
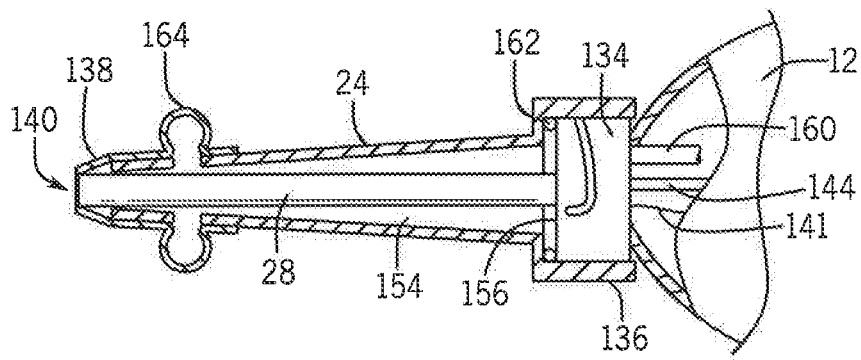
FIG. 16 is a cross-section along a vertical plane through the speculum and otoscope of FIG. 15 showing internal air passages for inflation of the collar.

Referring now to FIGS. 15 and 16, in yet a further alternative embodiment, the speculum 24 may have at its distal tip 26 a small toroidal balloon 164 coaxial about axis 22 that may be inflated and deflated to extend radially from the speculum 24 or to collapse against the speculum 24. This inflation and deflation may be through a channel 154 in the speculum 24 leading to a port 156. In this case the conduit 160 provides a source of pressurized air or release of pressurized air for the inflation and deflation operation. The balloon 164 may be constructed of the elastomeric material 138 also used for the window 140 formed at the same time during a dipping process. In this respect, the balloon 164 may be inflated once the speculum 24 is in place for the removal of debris or earwax from the ear, for example, as taught in U.S. Pat. No. 6,152,940 hereby incorporated by reference, albeit with the modification that the toroidal shape of the balloon 164 permits continued visualization through the window 140 unlike that of the cited reference. The conduit 160 may be provided with an external source of pressurized gas or may operate from an internal pressure reservoir as will be described below.

Figure 17:
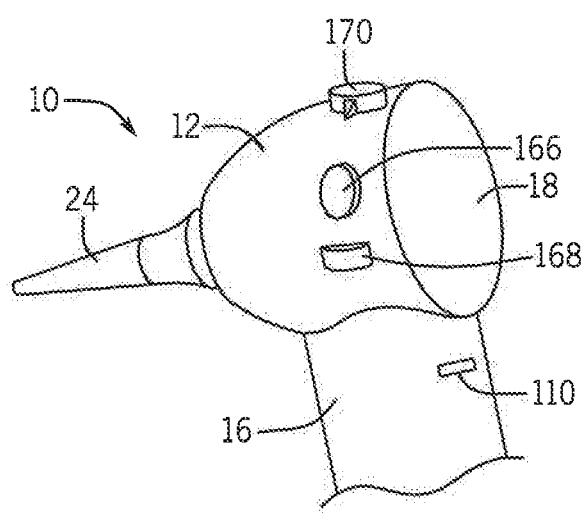
FIG. 17 is a figure similar to that of FIG. 7 showing the addition of a valve pump button and valve release button and a pump mode button allowing for generation of small amounts of stored pressurized air or relative vacuum within the housing of the otoscope.
Figure 18:
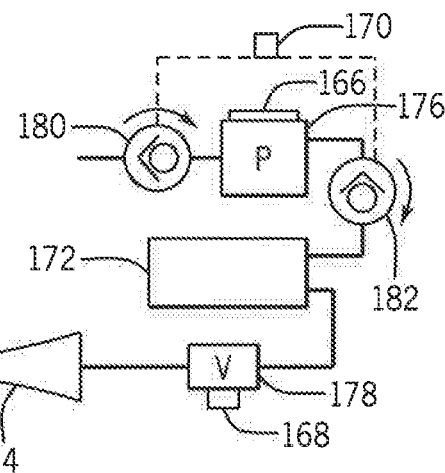
FIG. 18 is a schematic diagram of the pump system of FIG. 17 showing a system to provide for a reservoir of high or low-pressure air releasable after generation.

Features of these embodiments may be combined, for example, adding a clear window to either of the embodiments of FIGS. 11 and 13, Referring now to FIGS. 17 and 18, the housing 12 may be modified to provide for a pump button 166, a release button 168, and a valve direction knob 170 that allow an internal reservoir 172 within the housing 12 to be pressurized or evacuated using a pump 176 actuated by pump button 166. Once the reservoir 172 is charged, the vacuum or pressure may be released by valve button 168 controlling a valve 178 communicating through the speculum 24 with either the scoop 152 or balloon 164 discussed above. An input check valve 180 on the inlet side of the pump 76 and an output check valve 182 on the outlet side of the pump 176 may be simultaneously rotated in two different directions to provide either that the pump 176 evacuates the reservoir 172 or pressure rises in the reservoir 172. By pre-pumping the reservoir 172, a vacuum or pressure may be easily applied by the healthcare professional with little disruption of the housing 12 during use of the otoscope 10.

Figure 19:
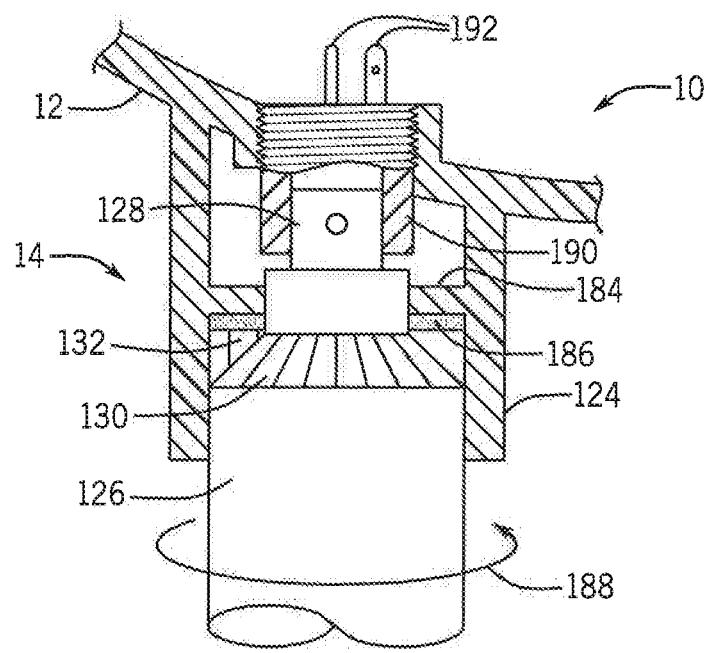
FIG. 19 is a partial cross-section through the housing of FIG. 1 showing engagement of the releasable handle to a display portion using a collar extending over the upper end of the handle for preventing inadvertent operation of a rheostat of the handle and providing an activation of the rheostat when the collar is installed.

Referring now to FIGS. 7 and 19, the collar 124 of the head portion 14 of the housing 12 may fit over the handle 126 and in particular over the rheostat operator 130 and rheostat operator button 132 to prevent inadvertent movement of these components during use of the otoscope 10. During installation of the collar 124 over the end of the handle 126, an internal collar ledge 184 extending radially inward over the rheostat operator 130 and having an elastomeric gripping material 186 on its lower surface may engage with the upper surface of the rheostat operator 130 and the rheostat operator button 132 to press the button 132 downward to release the rheostat operator for motion. A twisting of the handle 188 to engage connector 128 with mating connector 190 held in the head portion 14 will then rotate the rheostat operator 130 with respect to the handle 126 to turn the rheostat to its highest voltage position and retain it there during use of the otoscope 10.

Connector 128 and connector 190 may work with standard otoscope handles 126 using a connector system, for example, taught by U.S. Pat. Nos. 3,071,747, 1,516,133, and 2,469,857 hereby incorporated by reference. As noted, interconnection of the connectors 190 and 128 provides both mechanical connection between the handle 126 and the housing 12 and electrical connection with wiring terminals 192 of connector 190, the latter providing power to the system shown, for example, in FIG. 6 as battery 109 where connectors 190 and 128 provide connector system 115.

Figure 20:
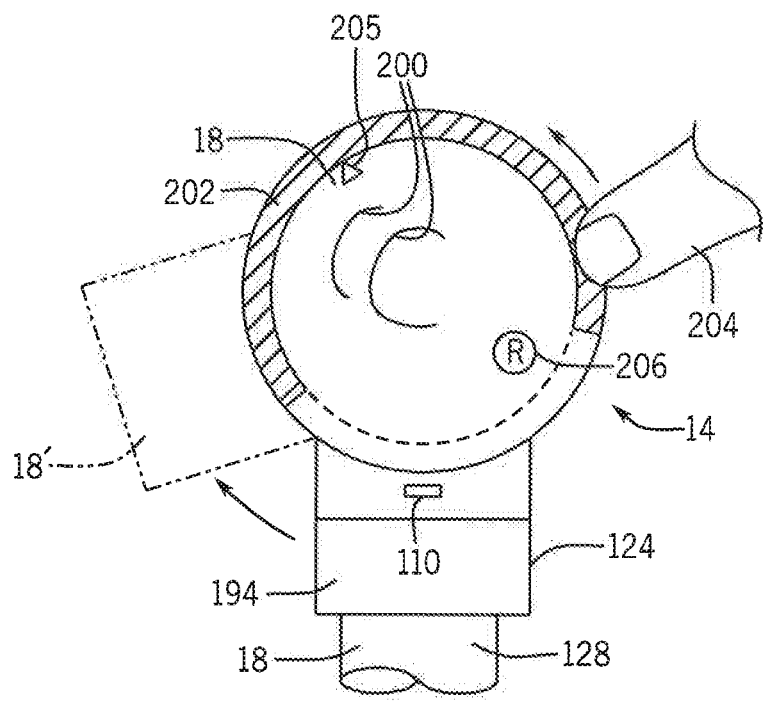
FIG. 20 is a rear elevational view of the otoscope of FIG. 1 showing the addition of non-image data to the image displayed on the display and a separable adapter for implementing the collar arrangement of FIG. 19.

Referring now to FIG. 20, the collar 124, ledge 184, elastomeric gripping material 186, and connector 190 may alternatively be placed in a releasable adapter 194 that may be releasably attached to the remainder of the head portion 14 so that the adapter 194 may be pre-installed on the handle 126 and a separate arbitrary connector system used to mechanically and electrically join the adapter 194 with the remainder of the head portion 14 and grip portion 16.

Referring still to FIG. 20, the circular display 18, for example, may be a touchscreen LCD or organic LED display such as minimizes obstruction of vision by the healthcare professional viewing the display 18 displaying a field of interest such as may depict a clinical image 200 of an eardrum and portions of the ear canal. A peripheral region of the display 18 may provide for non-image data of an arcuate bar display 202, for example, providing an arcuate band extending by varying angles about the center of the display 18 to indicate a magnitude and/or range of a variety of different quantities. In one embodiment, the arcuate length of the bar display 202 may represent a length of the video sequence of images acquired by the camera 30. Moving one's finger 204 around the arc of the bar display 202 allows selection of a particular still image from that video sequence for viewing in the manner of a video scrubbing operation. The bar display 202 may also indicate by its length a variety of different quantities, for example, battery charge. Alternatively, the arcuate length of the bar display 202 may indicate a range of battery charge states (0 to 100 percent), and a marker arrow 205 moving about the periphery may indicate a battery charge within that range. Generally, the invention contemplates that this peripheral region may be used for display purposes without interfering with the display clinical image 200.

A center region of the circular display 18 may also provide a touch sensitivity, for example, to allow a touch to trigger the taking of a snapshot of the given video when video recording is not enabled. A touch to the right of the display 18 may display non-image data of a right-side marker 206 indicating on the display 18 (and recorded in the stored images) that a particular story image is an image of the right ear. A corresponding a touch on the left side of the display 18 may provide a similar (but not shown) left marker. By placing this data around a periphery of the display 18, less important areas of clinical image 200 are covered while permitting simultaneous viewing of important areas of the clinical image 200 together with non-image data without the healthcare physician averting his or her eyes.

An accelerometer or inclinometer 107, discussed with respect to FIG. 16, may be used to deduce the orientation of the handle element at 18 or 18', for example, to rotate displayed non-image data such as the arcuate bar display 202 or the side marker 206 to maintain a standard orientation with respect to gravity and the user for these elements as displayed during use of the otoscope 10. During normal use, the displayed clinical image 200 always maintains the same orientation as the image structure in the ear; however, the recorded image may be adjusted upon storage by using the orientation derived from the inclinometer 107 to rotate that image so that it displays in the same orientation as if the otoscope 10 were held with a normal position of the grip portion 16 (directed generally downward). In this way, images viewed by an individual who is unaware of the actual orientation of the otoscope 10 during the image acquisition provide a standard orientation eliminating confusion. Thus, use of the inclinometer 107 to rotate the images before storage allows more flexibility in obtaining images without concern about their recorded orientation being confusing. Alternatively, the inclinometer 107 may be used to place an arrow marker (non-image data) in the image indicating the up direction.

Figure 21:
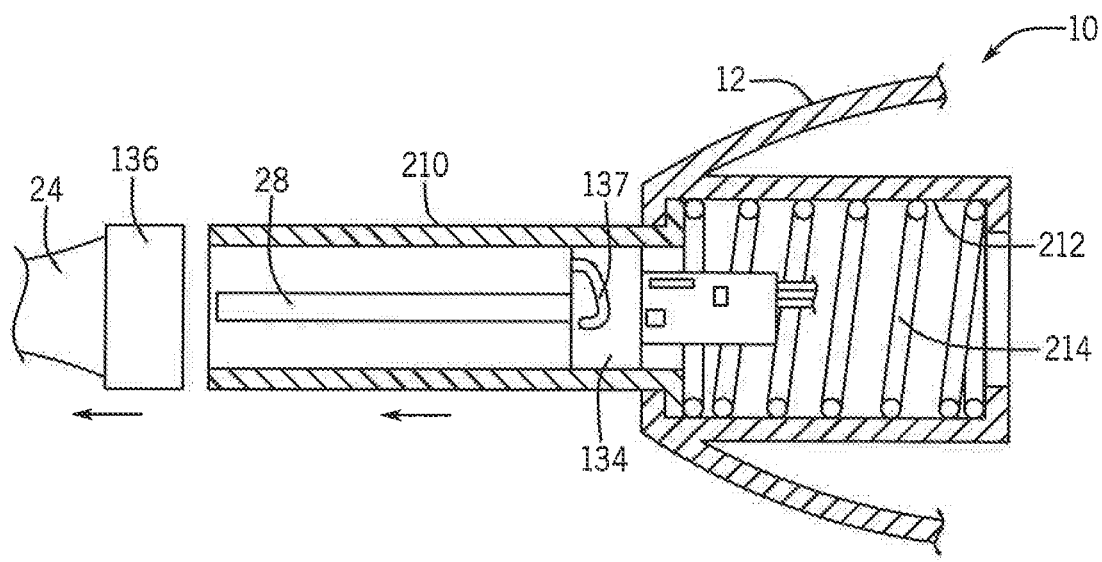
FIG. 21 is embodiment showing a spring-loaded collar that extends outward to protect the probe when the speculum is removed.

Referring now to FIG. 21, in one embodiment, a protective tubular sheath 210 may extend from the housing 12 around the probe 28 when the speculum 24 is removed or changed. This sheath 210 may pass around the outside of the boss 134 to be received within an internal pocket 212 within the housing. The sheath 210 may be biased outward toward the extended position as urged by a helical compression spring 214 captured in the pocket 212. The extension of the sheath 210 when the speculum 24 is removed prevents damage to the probe 28, for example, if the otoscope 10 were to be dropped. Contact between collar 136 and the distal end of the sheath 210 when the speculum 24 is attached presses the sheath 210 back into the housing 12 and out of the way.

Figure 22:
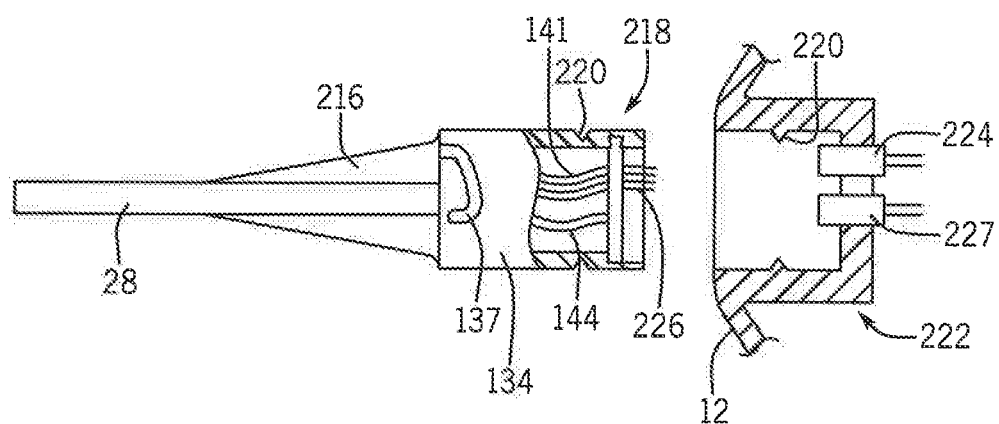
FIG. 22 is a partial cross-sectional view of the probe element of FIG. 7 allowing snap-in replaceability of the probe element in the event of damage and possible mitigation of damage through a snap-out of the probe element.

Referring now to FIG. 22, space between the inside surface of the speculum 24 (not shown in FIG. 21) and the probe 28 may contain one or more conforming ribs 216 or similar over-molded plastic supports having a generally trumpet shaped profile. These ribs 216 provide additional support and protection to the probe 28 and eliminate a visual impression that the probe 28 is a needle such as may be distressing to pediatric patients. The ribs 216 may be integrally molded with the boss 134 for extra strength. The boss 134 may be detachable from the structure of the housing 12, for example, providing a plug end 218 on the boss 134 releasably retained, for example, by snap elements 220 in a socket 222 affixed to the housing 12. The socket 222 may support an electrical connector 224 mating with a similar connector 226 supported by the plug end 218. Socket 222 may also support one or more high-powered LEDs 227 to be aligned with the fiber optics 144 when the plug end 218 is inserted into the socket 222. In this way, the probe 28 may be readily replaced if damaged or different styles or lengths of probes 28 can be installed. The amount of force necessary to remove the plug end 218 from the socket 222 may be set to allow these components to separate if the otoscope 10 is dropped minimizing damage. In one embodiment, the inclinometer 107 may be accelerometer-based and detect freefall of the otoscope 10 (by a near zero measured acceleration) and employ an electronic actuator (not shown) to release this connection further minimizing damage.

The boss 134 may also include the LEDs to simplify its replacement by requiring only electrical connections to the rest of the otoscope. The boss 134 may have its own threaded attachment or may be held in place by a threaded collar or the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

"Diameter" as used herein should not be understood to require a cylindrical or circular element but to simply describe a diameter of a circumscribing cylinder closely conforming to the element.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. An otoscope comprising:
a housing adapted for support by a hand of a healthcare professional with the housing in an inspection position adjacent to an outer ear of a patient; an elongate probe element having a proximal end supported by the housing so that a distal end of the elongate probe element may extend rigidly from the proximal end to the distal end along a linear axis into an ear canal of the patient; an electronic camera supported by the distal end of the elongate probe element for viewing into the ear canal when the distal end of the probe element is positioned in the ear canal of the outer ear; a circular electronic display communicating with the electronic camera and having a display area defining an outer circular periphery displaying an otoscope image taken by the electronic camera and spaced from the distal end of the elongate probe along the linear axis and centered along the linear axis to extend outwardly a substantially same distance at all angles perpendicular to the linear axis; and a processor executing a stored program for displaying non-otoscope image data in a peripheral ring about the otoscope image wherein the non-otoscope image data includes an arcuate bar display whose angular extent indicates data and wherein the arcuate bar is located against and conforming to an outer periphery of the circular electronic display.

2. The otoscope of claim 1 wherein the housing and the circular electronic display is circumscribed by a cone having an apex at the distal end of the probe and a conical angle of less than 45 degrees.

3. The otoscope of claim 1 wherein the circular electronic display extends less than 1.25 inch from the linear axis at all angles perpendicular to linear axis.

4. The otoscope of claim 1 wherein the circular electronic display provides a touchscreen for sensing touches on a surface of the circular electronic display wherein the arcuate bar display represents a video sequence of images taken from the electronic camera and wherein a touch along the arcuate bar display selects an image from the video sequence for display.

5. The otoscope of claim 1 further including a display indicating a left or right ear recorded indicator to the image.

6. An otoscope comprising: a housing adapted for support by a hand of a healthcare professional with the housing in an inspection position adjacent to an outer ear of a patient; an elongate probe element having a proximal end supported by the housing so that a distal end of the elongate probe element may extend rigidly from the proximal end to the distal end along a linear axis into an ear canal of the patient; an electronic camera supported by the distal end of the elongate probe element for viewing into the ear canal when the distal end of the probe element is positioned in the ear canal of the outer ear; and a circular electronic display communicating with the electronic camera and having a display area defining an outer circular periphery displaying an otoscope image taken by the electronic camera and spaced from the distal end of the elongate probe along the linear axis and centered along the linear axis to extend outwardly a substantially same distance at all angles perpendicular to the linear axis; a processor executing a stored program for displaying non-otoscope image data in a peripheral ring about the otoscope image; an electronic inclinometer for changing at least one of an orientation of the non-otoscope image data on the circular electronic display and a recorded image according to a deduced gravitational vector.

7. The otoscope of claim 1 wherein the housing provides a display portion holding the circular electronic display and elongate probe, and a handle portion extending away from the linear axis to be held by a healthcare professional and wherein the display portion is mechanically and electrically releasably attachable to the handle portion by means of a twist lock coupling.

8. An otoscope comprising: a housing adapted for support by a hand of a healthcare professional with the housing in an inspection position adjacent to an outer ear of a patient; an elongate probe element having a proximal end supported by the housing so that a distal end of the elongate probe element may extend rigidly from the proximal end to the distal end along a linear axis into an ear canal of the patient; an electronic camera supported by the distal end of the elongate probe element for viewing into the ear canal when the distal end of the probe element is positioned in the ear canal of the outer ear; and a circular electronic display communicating with the electronic camera and having a display area defining an outer circular periphery displaying an otoscope image taken by the electronic camera and spaced from the distal end of the elongate probe along the linear axis and centered along the linear axis to extend outwardly a substantially same distance at all angles perpendicular to the linear axis; wherein the housing provides a display portion holding the circular electronic display and elongate probe, and a handle portion extending away from the linear axis to be held by a healthcare professional and wherein the display portion is mechanically and electrically releasably attachable to the handle portion by means of a twist lock coupling; wherein the handle portion provides an operator controlling electrical power delivered to the display portion and wherein the handle portion provides a collar fitting over the operator to prevent movement of the operator.

9. The otoscope of claim 8 wherein the collar portion includes a rheostat engagement surface turning the operator to a full power position with rotation of the twist lock coupling for engagement.

10. The otoscope of claim 8 wherein the display portion includes a releasable adapter portion releasably receiving the handle portion.

11. An otoscope comprising: a housing adapted for support by a hand of a healthcare professional with the housing in an inspection position adjacent to an outer ear of a patient; an elongate probe element having a proximal end supported by the housing so that a distal end of the elongate probe element may extend rigidly from the proximal end to the distal end along a linear axis into an ear canal of the patient; an electronic camera supported by the distal end of the elongate probe element for viewing into the ear canal when the distal end of the probe element is positioned in the ear canal of the outer ear; and a circular electronic display communicating with the electronic camera and having a display area defining an outer circular periphery displaying an otoscope image taken by the electronic camera and spaced from the distal end of the elongate probe along the linear axis and centered along the linear axis to extend outwardly a substantially same distance at all angles perpendicular to the linear axis; a set of light sources supported by the distal end of the elongate probe element for illuminating the ear canal when the distal end of the probe element is positioned in the ear canal; a replaceable tubular sheath sized to fit within in the ear canal and to receive the elongate probe element therein, the distal end of the tubular sheath providing a transparent window covering allowing imaging therethrough and a proximal end of the tubular sheath providing a connection to the housing providing a spring biasing of the window against the distal end of the probe element; wherein the proximal ends of the light sources and electronic camera are configured to eliminate a path of internal reflection between the light sources and the electronic camera from the window when the window is pulled against the distal end of the probe element.

12. The otoscope of claim 11 wherein the transparent window is an elastic cot and the connection to the housing stretches the elastic cot over the electronic camera to provide a transparent covering to the camera allowing imaging therethrough.

13. A disposable speculum for an otoscope of a type having:
a housing adapted for support by a hand of a healthcare professional with the housing in an inspection position adjacent to an outer ear of a patient; an elongate probe element having a proximal end supported by the housing so that a distal end of the elongate probe element may extend rigidly from the proximal end to the distal end along a linear axis into an ear canal of the patient; an electronic camera supported by the distal end of the elongate probe element for viewing into the ear canal when the distal end of the probe element is positioned in the ear canal of the outer ear; and a circular electronic display communicating with the electronic camera and having a display area defining an outer circular periphery displaying an otoscope image taken by the electronic camera and spaced from the distal end of the elongate probe along the linear axis and centered along the linear axis to extend outwardly a substantially same distance at all angles perpendicular to the linear axis; a set of light sources supported by the distal end of the elongate probe element for illuminating the ear canal when the distal end of the probe element is positioned in the ear canal; wherein the proximal ends of the light source and electronic camera are configured to eliminate a path of internal reflection between the light source and the electronic camera from a window when the window is pulled against the distal end of the probe element, the disposable speculum comprising: a replaceable sheath providing substantially inelastic sidewalls are sized to fit within the ear canal and to receive the elongate probe element therein, the distal end of the tubular sheath providing a transparent window covering allowing imaging therethrough and a proximal end of the tubular sheath providing a connection to the housing providing a spring biasing of the replaceable tubular sheath to pull the window against the distal end of the probe element.

14. The otoscope of claim 1 further comprising:
a tubular sheath sized to fit within the ear canal and to receive the elongate otoscope probe element therein, wherein the distal end of the tubular sheath is covered by an elastic cot and wherein a proximal end of the tubular sheath is adapted to engage the otoscope to stretch the elastic cot over the electronic camera to provide a transparent covering over the camera allowing imaging therethrough.

15. The otoscope of claim 1 further comprising:
a tubular sheath sized to fit within the ear canal and to receive the elongate otoscope probe element therein, wherein the distal end of the tubular sheath provides a tool extending axially beyond the distal end of the probe element for engaging objects within an ear within a field of view of the camera.

16. The otoscope of claim 15 wherein the tool element is malleable to be formed into a curve with respect to an axis of the tubular sheath and to retain that curvature.

17. The otoscope of claim 15 wherein the tool element provides a scoop communicating with a channel connectable to a vacuum source.

18. The otoscope of claim 1 further comprising: a microphone; and a processor executing a program stored in non-transient medium and communicating with the electronic camera, the microphone, and the circular electronic display to operate in a first mode to provide a dynamic image on the display indicating the view from the electronic camera and in a second mode, triggered by a user's voice received by the microphone, to capture a static image on the display indicating a view from the electronic camera at a time of the trigger.

19. The otoscope of claim 1 wherein the housing and the circular electronic display is circumscribed by a cone having an apex at the distal end of the probe and a conical angle of less than 60 degrees.

20. The otoscope of claim 1 wherein the otoscope image has an outer circular periphery.

* * * * *